United States Patent [19]

Reeder

[11] Patent Number: 4,668,214

[45] Date of Patent: May 26, 1987

[54] METHOD OF WASHING RED BLOOD CELLS

[75] Inventor: Gary D. Reeder, Englewood, Colo.

[73] Assignee: Electromedics, Inc., Englewood, Colo.

[21] Appl. No.: 872,015

[22] Filed: Jun. 9, 1986

[51] Int. Cl.[4] .................. B04B 11/02; B01D 21/26
[52] U.S. Cl. .............................. 494/37; 494/27
[58] Field of Search ............ 494/17, 22, 23, 27, 494/37; 210/516, 772, 780, 782; 604/6

[56] References Cited

U.S. PATENT DOCUMENTS

| 3,145,713 | 8/1964 | Latham, Jr. | 604/6 |
| 4,086,924 | 5/1978 | Latham, Jr. | 604/6 |
| 4,187,979 | 2/1980 | Cullis et al. | 604/6 |
| 4,269,718 | 5/1981 | Persidsky | 210/516 |
| 4,285,464 | 8/1981 | Latham, Jr. | 604/6 |
| 4,303,193 | 12/1981 | Latham, Jr. | 494/27 |
| 4,482,342 | 11/1984 | Lueptow et al. | 494/27 |

Primary Examiner—Robert W. Jenkins
Assistant Examiner—Corinne Reinckens

[57] ABSTRACT

A method of cleaning red blood cells which have been separated from undesirable components of blood in a centrifugal separating chamber includes the steps of pulsating a washing solution through the red blood cells in an alternating high flow rate/low flow rate sequence so as to alternately agitate the red cells for optimal cleaning and stabilize the red cells to prevent a flushing of the cells from the separation chamber.

5 Claims, 6 Drawing Figures

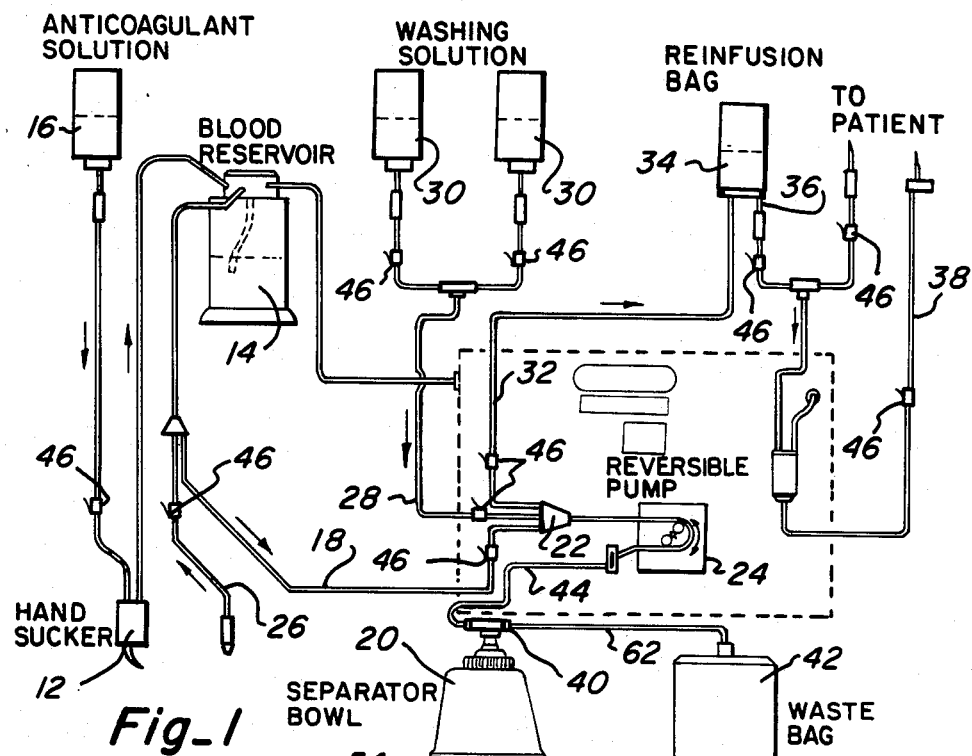
Fig_1
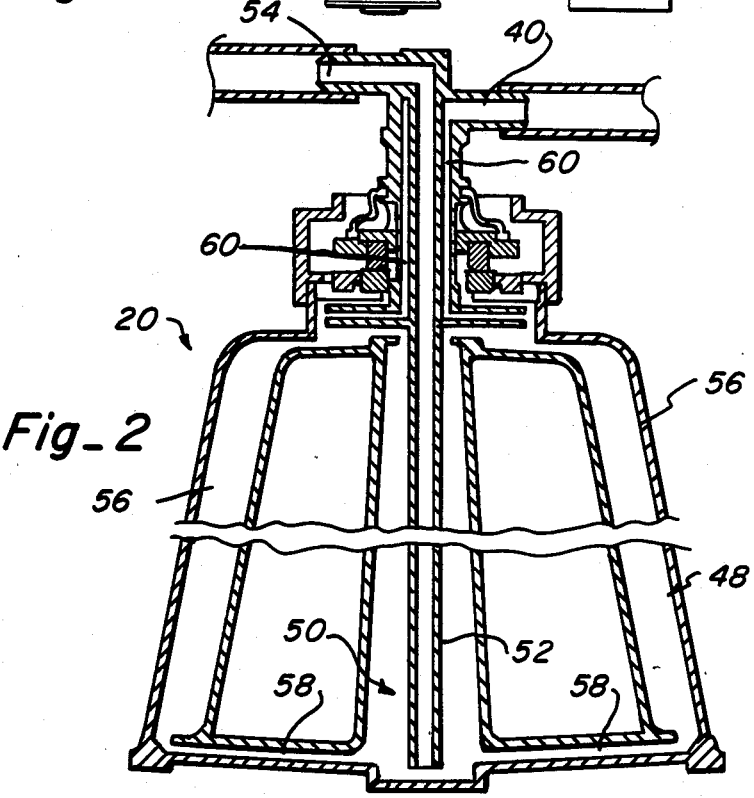
Fig_2

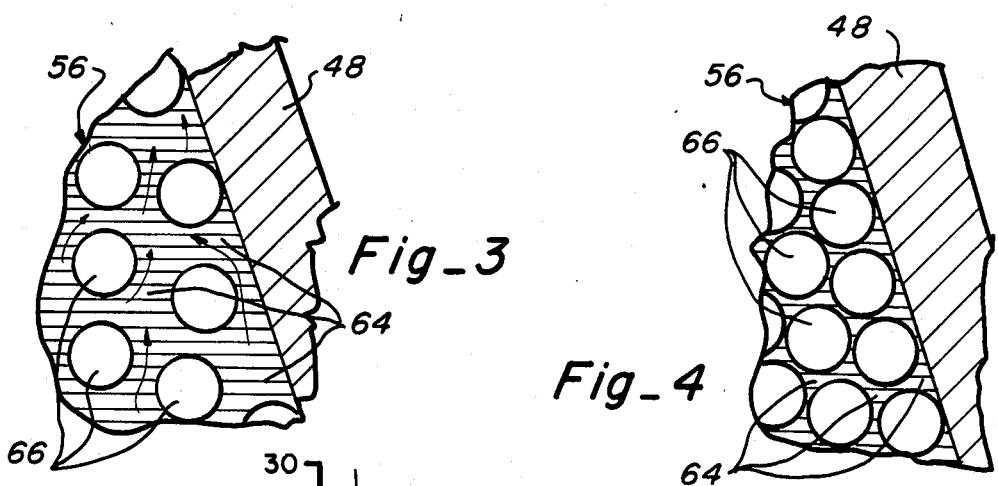
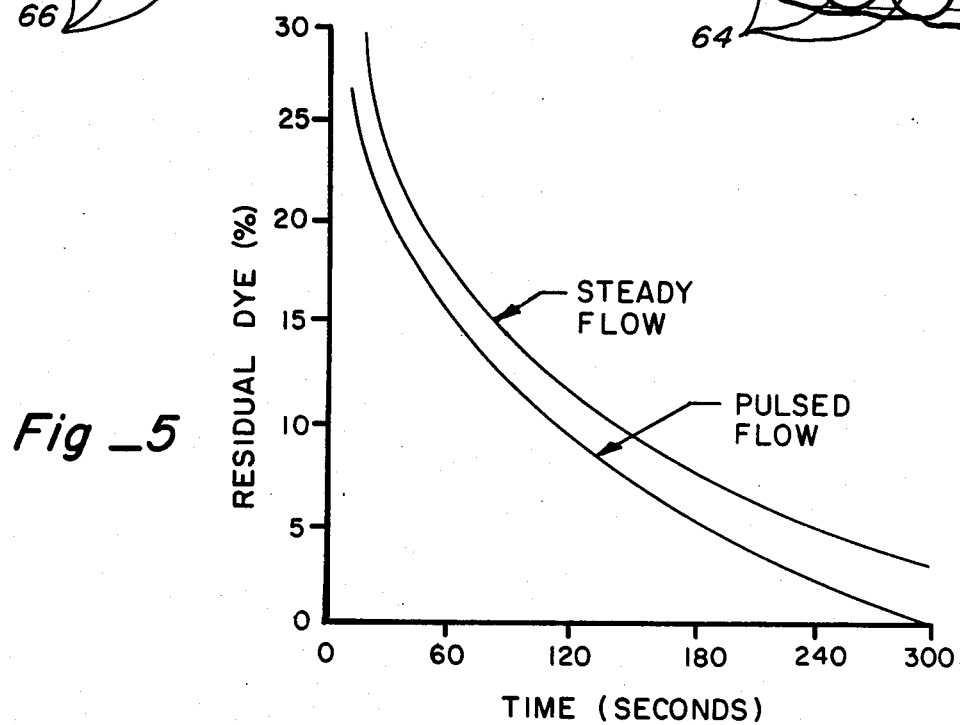
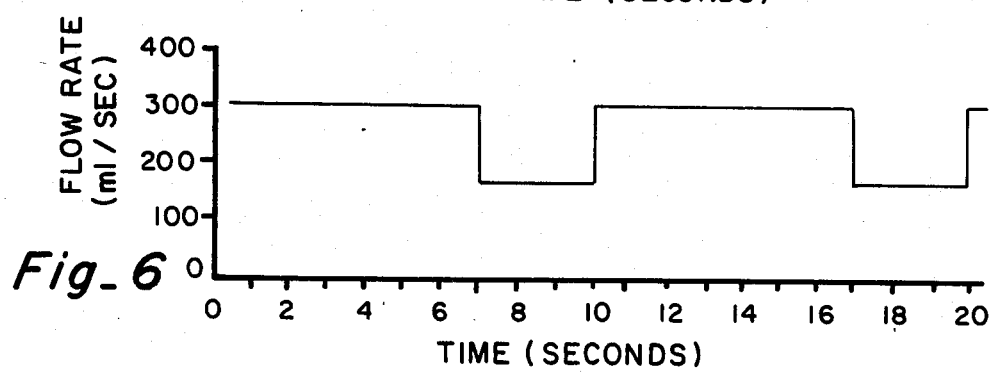

METHOD OF WASHING RED BLOOD CELLS

BACKGROUND OF THE INVENTION

1. Field of the Invention

This invention relates generally to blood transfusions or reinfusions and more particularly to a method of removing undesirable elements from whole blood once it has been removed from a patient and prior to its being reinfused or transfused.

2. Description of the Prior Art

Whole human blood includes at least three types of specialized cells. These are the red blood cells, white blood cells and platelets. All of these cells are suspended in plasma, a complex aqueous solution of proteins and other chemicals.

When removing blood from a donor for homologous transfusion, for reinfusion or when obtaining blood for plasmapheresis, and/or salvaging blood from a body cavity or wound site, it is important to remove the undesirable elements from the blood before reinfusing or transfusing the blood into a patient. The undesirable elements that must be removed include plasma, activated clotting factors and/or byproducts of coagulation, drugs, cellular debris, platelets and leukocytes, otherwise referred to as white blood cells. The only element of the blood which remains after the removal of the undesirable elements are the red blood cells, which are the desired element for reinfusion or transfusion.

Numerous systems have been developed for cleaning whole blood by removing the undesirable elements, an example of which is disclosed in U.S. Pat. No. 4,086,924 issued to Latham, Jr. These systems include means for removing the blood from a patient, adding an anticoagulant to the blood, separating the various components of the blood usually in a centrifugal separator, washing the desirable red blood cell component which is retained in the separator with a saline solution, and then reinfusing the clean red blood cells into the patient from whom the blood was drawn or transfusing the blood into a donor patient.

The separation and washing process, as mentioned above, is normally accomplished in a centrifugal separator wherein the whole blood, including the anticoagulant, is introduced through a central column of a rotating bowl so that the blood will flow to the outer edge of the bowl and subsequently upwardly along a circumferential wall of the bowl until the lighter elements are discharged through an outlet provided near the top of the bowl. The red blood cells being the heaviest component of whole blood remain in the bowl for the longest period of time so that the lighter undesirable elements are discharged before the red blood cells fill the separating bowl. Once the bowl is substantially full of red blood cells, the cells have become compacted against the circumferential wall of the bowl and portions of the plasma remain trapped in the interstitial spaces between the red blood cells. In order to remove the plasma from the spaces between the red blood cells, it has been common practice to pass a saline solution through the centrifugal separator to wash the plasma out of the interstitial spaces between the cells.

One problem with this prior art system of washing the red blood cells with a constant flowing saline solution is that the flow rate necessary to rapidly wash the red blood cells is also sufficient to carry the red blood cells through the outlet at the top of the bowl thereby washing valuable blood cells out of the separator making the system inefficient. On the other hand, if a constant flow rate of saline passing through the separator is not great enough to agitate the blood cells, it will not adequately clean the cells as it will not flush the plasma out of the spaces between the red blood cells in a short period of time. In other words, the red blood cells being compacted by the centrifugal forces of the separator bowl require a relatively high flow rate of saline to separate the blood cells so that the plasma and other undesirable elements can be removed, but this relatively high flow rate is detrimental in that it carries valuable red blood cells out of the separator bowl.

It is accordingly a primary object of the present invention to provide a new and improved method of cleaning red blood cells which is more efficient and does not result in a significant loss of red blood cells.

It is another object of the present invention to provide a method of cleaning red blood cells which utilizes a greater volume of wash solution in a given period of time so as to more thoroughly clean the red blood cells without a significant loss thereof.

SUMMARY OF THE INVENTION

The present invention relates to an improved method of washing red blood cells in a centrifugal separator bowl and operates under the premise of optimizing the quantity of washing solution passing through the separator bowl in a given period of time.

This is accomplished by pulsating the flow of the washing solution through the separator utilizing relatively high and relatively low flow rates. In this manner, the red blood cells which are typically compacted by the centrifugal force of the separator bowl are agitated during the high flow rate portion of a cycle and allowed to again compact during the low flow rate portion of the cycle. The red blood cells are therefore agitated by the high flow rate washing solution, but only for a short period of time so that they are not carried out of the separating bowl by the washing solution but rather are allowed to settle and again become compacted before the washing solution can carry the red blood cells from the separator bowl. However, during the high flow rate portion of a cycle, the red blood cells are separated sufficiently enough to allow the washing solution to flush the undesirable elements from the interstitial spaces between the red blood cells and then carry these lighter undesirable elements from the separator bowl before the red blood cells can be removed from the bowl. During the low flow rate portion of a cycle, the washing solution continues to carry the undesirable elements out of the separator bowl, but allows the heavier red blood cells to remain in the bowl.

By alternating high and low flow rates in a pulsating cyclical manner, the high flow rate can be greater than the uniform flow rates used in the prior art without the loss of red blood cells due to the fact that the high flow rate is only operative for short periods of time. However, by utilizing such unusually high flow rates combined with relatively low flow rates, a greater volume of washing solution can be passed through the red blood cells in a given period of time to effect a more thorough cleaning of the red cells. This, of course, provides for a more efficient cleaning process.

Other aspects, features and details of the present invention can be more completely understood by reference to the following detailed description of a preferred embodiment, taken in conjunction with the drawings, and from the appended claims.

BRIEF DESCRIPTION OF THE DRAWINGS

FIG. 1 is a diagrammatic representation of an apparatus used for cleaning blood utilizing the method of the present invention.

FIG. 2 is a vertical fragmentary section taken through a centrifugal separator bowl utilized in the apparatus illustrated in FIG. 1.

FIG. 3 is a fragmentary section of a portion of the separator bowl illustrated in FIG. 2 with a diagrammatic representation of red blood cells as they would be situated during a high flow rate condition of washing solution.

FIG. 4 is a fragmentary section similar to FIG. 3 with a diagrammatic representation of red blood cells as they would be situated during a low flow rate condition of washing solution.

FIG. 5 is a graph representing two tests wherein dye was removed as an impurity in whole blood by a prior art steady flow of washing solution in one test and a pulsed flow of the same washing solution in a second test.

FIG. 6 is a graph representing the method of injecting washing solution into a compacted group of red blood cells in accordance with the teachings of the present invention plotting the flow rate of the washing solution against time.

DESCRIPTION OF THE PREFERRED EMBODIMENT

There are a number of systems available for treating whole blood removed from a patient so as to remove the undesirable elements from the whole blood, leaving clean red blood cells either for reinfusion back into the patient or for transfusion into another patient. A sample of such a system 10 is diagrammatically illustrated in FIG. 1 with this particular system being equipped to remove blood from a body cavity or wound site. The system illustrated in FIG. 1 is manufactured by Dideco S.p.A. of Mirandola, Italy under the designation Autotrans BT 795/P.

Referring to FIG. 1, it will be appreciated that a hand sucker 12 is utilized to collect blood from a body cavity or wound site by a vacuum source which is operative through a blood reservoir 14 such that an anticoagulant solution 16 is also drawn into the supply of whole blood before it enters the blood reservoir. An outlet line 18 from the blood reservoir passes to a centrifugal separator 20 through a trifurcated connector 22 and a reversible pump 24 and is in fluid communication with a connection line 26 that may be connected to another device such as an oxygenator in order to salvage the blood from that device. The three inlet ports of the trifurcated connector 22 are connected respectively to the outlet line 18 from the blood reservoir 14, an outlet line 28 from a pair of washing agent or solution containers 30, and the inlet line 32 to a reinfusion bag 34. An outlet 36 from the reinfusion bag 34 is connected through a tubular system 38 for reinfusing the clean blood to a patient in a conventional manner. An outlet 40 from the separator bowl 20 is connected to a waste bag 42 where the undesirable elements of the blood which are separated from the red blood cells can be collected.

The operation of the separator bowl 20 will be described in more detail hereinafter, but it is important to note that the reversible pump 24, in one mode, is effective in withdrawing blood from the blood reservoir 14 and pumping it through an inlet line 44 into the separator bowl 20 and, in another mode, the pump 24 can be reversed to withdraw blood from the separator bowl 20 through the same inlet line 44 and pump it into the reinfusion bag 34. Selectively operable clamps 46 are positioned on the various liquid flow lines to open and close the lines as necessary for operation of the system.

A vertical section through a typical centrifugal separator bowl 20 of the type used in the system shown in FIG. 1 is illustrated in FIG. 2. The separator bowl will not be described in a lot of detail due to the fact that it is a commercially available item manufactured by Dideco S.p.A. of Mirandola, Italy under the designation B.T. Bowl. Suffice it to say that the separator bowl 20 includes a generally bellshaped body 48 defining a central cavity 50 into which an inlet tube 52 extends so as to open at the lowermost end of the cavity 50. The inlet tube 52 has an inlet opening 54 connected to the inlet line 44 from the reversible pump 24 so that whole blood can be pumped into the separator bowl through the inlet tube. The body 48 of the separator bowl also includes an outer circumferential separating chamber 56 connected to the central cavity 50 by a circular disc-shaped channel 58 extending along the bottom of the bowl. With this arrangement, as the separator bowl is rotated by a driving assembly (not shown), blood entering the central cavity through the inlet tube 52 is dispersed centrifugally through the circular channel 58 at the bottom of the bowl and flows into the separating chamber 56 at the outer circumference of the bowl. The separating chamber is connected via a generally cylindrical passageway 60 to the outlet 40 which receives one end of a flow line 62 passing directly to the waste bag 42.

In operation of the device, blood which has been withdrawn from a patient through the hand sucker 12 and mixed with an anticoagulant solution 16 before entering the blood reservoir 14 is drawn from the blood reservoir by the reversible pump 24 via the line 18 and the blood is pumped into the separator bowl 20 through the inlet line 44. Of course, while the blood is being drawn from the blood reservoir, the line 28 from the washing solution containers 30 and the line 32 passing to the reinfusion bag 34 from the trifurcated connector 32 are clamped off by clamps 46 so that the reversible pump is only effective in withdrawing blood from the blood reservoir and pumping it into the centrifugal separator bowl.

As the blood is pumped into the separator bowl 20, the bowl is rotated at a constant predetermined RPM, causing the blood to disperse through the circular channel 58 to the separating chamber 56 of the bowl. In the separating chamber, the lighter components of blood, namely the plasma, platelets, leukocytes (white blood cells) and any drugs or cellular debris will be displaced toward the center of the separator and due to the shape of the separator will rise to the top of the separating chamber while the heavier red blood cells remain adjacent to the outer wall of the separating chamber. Continued pumping of whole blood into the separator will cause the undesirable lighter components of the blood as well as any extraneous material to pass upwardly through the cylindrical outlet channel 60 and subsequently through the outlet 40 of the separator bowl and into the waste bag 42. Within a reasonably short period of time, the separating chamber 56 is substantially full of red blood cells which are typically compacted against the outer wall of the separation chamber due to the centrifugal force in the separator bowl. The compaction of the red blood cells leaves interstitial spaces 64 (FIGS. 3 and 4) between the red blood cells (erythrocytes) 66 with these spaces typically being filled with plasma. As mentioned previously, it is desirable to remove the plasma from the interstitial spaces 64 so that the blood being returned to the patient will satisfy predetermined standards for blood cleanliness. The present invention is concerned with obtaining a highly efficient removal of the plasma from the interstitial spaces between the red blood cells.

In the prior art usage of a system of the type illustrated in FIG. 1, after the undesirable elements have been removed from the whole blood so that the separating chamber is substantially full of red blood cells 66, the flow line 18 from the blood reservoir is closed and the flow line 28 from the washing solution containers, which typically carry a solution of saline, is opened so that the saline is pumped into the separator bowl 20 through the inlet line 44.

As mentioned previously, the red blood cells 66 in the separating chamber 56 are normally compacted due to the centrifugal force applied thereto, but the saline solution if pumped into the separating bowl at a high enough flow rate will agitate the blood cells and separate them so that the washing solution is effective in flushing the plasma out of the interstitial spaces between the cells. The washing solution is lighter than the red blood cells so that it carries the plasma through the outlet of the separator bowl to the waste bag leaving the clean red blood cells in the separator.

It has been found, however, that flow rates of washing solution which are adequate to agitate the red blood cells sufficiently to separate them are also adequate to carry some of the red blood cells out of the separator bowl. Conversely, flow rates of washing solution which are low enough not to carry the red blood cells out of the separating bowl are also not adequate to agitate the red blood cells and therefore do not sufficiently remove the plasma from the interstitial spaces between the red blood cells without a prolonged wash.

As will be appreciated, the higher the centrifugal force applied to the red blood cells, the smaller the interstitital spaces, within physical limits of cell size. The centrifugal forces are opposed by the forces created by the washing solution flowing through the cell pack and separating the red blood cells. Thus, the packing ability of the system is inversely related to the rate of washing solution flow and directly related to the rotational speed of the bowl. The use of relatively high washing solution flow rates will, therefore, destabilize the cell pack with unnecessary loss of red blood cell product if sustained for a very long period of time.

An important feature of the present invention is the intentional alteration of the balance between these opposing forces, permitting momentary destabilization of the red blood cell pack, so as to widen the interstitial spaces between the cells and improve the dilution of the interstitial plasma. This is accomplished by pulsating the flow of washing solution through the separation chamber 56 by introducing the washing solution at a relatively high flow rate for a given period of time and then lowering that flow rate to a relatively low flow rate. The high flow rate must be sufficient to agitate the red blood cells 66 and thereby separate them to increase the size of the interstitial spaces 64 between the cells while the low flow rate must be low enough so that it does not carry red blood cells out of the separating chamber and pass them to the waste bag 42. Thus, during a low flow portion of a low flow/high flow cycle, the red blood cells will restabilize in a somewhat compacted relationship and will not be flushed from the separator bowl 20 with the undesirable components of the blood.

Due to the fact that the washing of the red blood cell pack is achieved by progressive dilution of the plasma, the purity or cleanliness of the final red blood cell product is dependent upon the volume of washing solution passing through the red blood cells and the effectiveness of its distribution throughout the cell pack. With the method of the present invention of pulsating the washing solution, a higher volume of washing solution can be passed through the cell pack in a given period of time than is presently possible with current constant flow systems and, in addition, the efficiency of the cleaning process is optimized by alternately agitating and allowing recompaction of the red blood cells.

As an illustration of the effectiveness of the present invention, two tests were conducted on whole blood, which had been infused with a dye, to determine how long it took for the dye to be removed using, in one test, the current state of the art steady flow washing system and, in the second test, the pulsating system of the present invention. By reference to the graph in FIG. 5 illustrating the results of the tests, it will be appreciated that the pulsating flow system of the present invention reduced the amount of residual dye in the blood to a lower level than that attainable with the steady flow system during any given time interval. Accordingly, if the accepted level of impurity in the blood (in this case dye) was 5%, it will be appreciated from the graph in FIG. 5 that the pulsating system achieved this level of purity in 180 seconds whereas the steady flow system of the prior art did not achieve this result for nearly 240 seconds.

In obtaining the results illustrated in the graph of FIG. 5, the steady flow rate of washing solution (which was a saline solution) was 200 milliliters per minute while the pulsating test was conducted utilizing a high flow rate of 300 milleters per minute and a low flow rate of 175 milliliters per minute for a net flow rate of 264 milliliters per minute, with the low flow rate duration being three seconds of each tensecond cycle and the high flow rate duration occupying the remaining seven seconds. In each test the rate of rotation of the separating bowl was 5000 RPM.

A graph of the pulsating method of the present invention is illustrated in FIG. 6 plotting the flow rate of the washing solution against time for the example illustrated in FIG. 5. It is to be understood that there are many variables of flow rates and time durations which will effectively wash compacted red blood cells with the particular flow rates and time durations set forth in the above example of FIGS. 5 and 6 being merely illustrative.

FIG. 3 is a diagrammatic representation of a plurality of red blood cells 66 in the separating chamber of the separating bowl during the high flow rate portion of a cycle. It will therein be appreciated that the cells 66 are separated enough so that the saline solution can freely pass therebetween and flush undesirable elements, such as plasma, from the spaces 64 between the cells. During a low flow rate portion of a cycle, the red cells are more compacted in a manner similar to that diagrammatically illustrated in FIG. 4, wherein it will be appreciated that the space between the red cells are much smaller thereby restricting, and in some cases, precluding the flow of saline solution through the cell pack.

Although the method of the present invention has been described with a certain degree of particularity, it is understood that the present disclosure has been made by way of example, and that changes in detail or structure may be made without departing from the spirit of the invention, as defined in the appended claims.

I claim:

1. A method of separating red blood cells from undesirable elements in blood and washing the red blood cells in a centrifugal separator having an inlet, an outlet, and a separating chamber, comprising the steps of:
   introducing whole blood through said inlet into the separating chamber,
   centrifugally separating the red blood cells from the undesirable elements in the blood in the separating chamber and releasing the undesirable elements from the chamber, and
   washing the red blood cells in the chamber by introducing a washing agent into the chamber in a cyclical manner with each cycle including a relatively fast and a relatively slow flow rate of the washing agent.

2. The method of claim 1 wherein the relatively fast flow rate is adequate to agitate and separate the red blood cells.

3. The method of claim 2 wherein the relatively slow flow rate is insufficient to carry red blood cells out of the chamber through said outlet.

4. The method of claim 3 wherein said fast flow rate is sufficient for the washing agent to carry red blood cells out of said chamber through said outlet but the time period of the fast flow rate is less than required for the washing agent at said fast flow rate to carry red blood cells out of the chamber through said outlet.

5. A method of separating red blood cells from the other whole blood components and washing the red blood cells in a centrifugal separator having an inlet, an outlet, and a separating chamber, comprising the steps of:
   introducing whole blood through said inlet into the separating chamber,
   centrifugally separating the red blood cells from the other whole blood components in the separating chamber and releasing the other whole blood components from the chamber, and
   washing the red blood cells in the chamber by alternately agitating the red blood cells with a washing agent by passing the washing agent through the chamber at a relatively high flow rate and stabilizing the red blood cells by passing the washing agent through the chamber at a relatively slow flow rate.

* * * * *